United States Patent
Reinke et al.

(10) Patent No.: US 6,985,775 B2
(45) Date of Patent: Jan. 10, 2006

(54) METHOD AND APPARATUS FOR SHUNTING INDUCED CURRENTS IN AN ELECTRICAL LEAD

(75) Inventors: James D. Reinke, Maple Grove, MN (US); Jeffrey D. Wilkinson, Vadnais Heights, MN (US); Ron Kalin, New Hope, MN (US); Laurie D. Foerster, Mound, MN (US); Volkert A. Zeijlemaker, Landgraaf (NL)

(73) Assignee: Medtronic, Inc., Minneapolis, MN (US)

(*) Notice: Subject to any disclaimer, the term of this patent is extended or adjusted under 35 U.S.C. 154(b) by 511 days.

(21) Appl. No.: 10/059,601

(22) Filed: Jan. 29, 2002

(65) Prior Publication Data

US 2003/0144716 A1 Jul. 31, 2003

(51) Int. Cl.
*A61N 1/05* (2006.01)
(52) U.S. Cl. ..................................... 607/116
(58) Field of Classification Search ........ 607/115–116, 607/119, 122–123
See application file for complete search history.

(56) References Cited

U.S. PATENT DOCUMENTS

| 4,320,763 | A | 3/1982 | Money | 607/9 |
|---|---|---|---|---|
| 5,217,010 | A | 6/1993 | Tsitlik et al. | 128/419 PG |
| 5,324,311 | A * | 6/1994 | Acken | 607/37 |
| 5,325,870 | A | 7/1994 | Kroll et al. | 607/122 |
| 5,366,496 | A | 11/1994 | Dahl et al. | 607/132 |
| 5,629,622 | A | 5/1997 | Scampini | 324/247 |
| 5,697,958 | A | 12/1997 | Paul et al. | 607/31 |
| 5,722,998 | A | 3/1998 | Prutchi et al. | 607/30 |
| 5,824,029 | A | 10/1998 | Weijand et al. | 607/122 |
| 6,101,417 | A | 8/2000 | Vogel et al. | 607/30 |
| 6,711,443 | B2 * | 3/2004 | Osypka | 607/122 |
| 6,738,672 | B2 * | 5/2004 | Schulman et al. | 607/116 |
| 6,871,091 | B2 * | 3/2005 | Wilkinson et al. | 607/2 |

FOREIGN PATENT DOCUMENTS

EP    0 778 048 A1    6/1997

* cited by examiner

*Primary Examiner*—Carl Layno
(74) *Attorney, Agent, or Firm*—Michael C. Soldner; Girma Wolde-Michael (57) ABSTRACT

An electrical lead end cap includes a body defining a bore therein capable of receiving and retaining an end of an electrical lead and a connector capable of electrically coupling conductors leading to at least two electrodes. A method includes routing an electrical current induced in an electrical lead conductor disposed within body tissue to a plurality of electrodes, electrically coupled with the body tissue, via a circuit within an end cap attached to the electrical lead.

29 Claims, 7 Drawing Sheets

1402 — ROUTING AN ELECTRICAL CURRENT INDUCED IN ONE OR MORE CONDUCTORS OF A LEAD BETWEEN ONE OR MORE ELECTRODES ELECTRICALLY COUPLED TO BODY TISSUE VIA A CIRCUIT WITHIN AN END CAP ATTACHED TO THE ELECTRICAL LEAD

FIG. 15

1402 — ROUTING AN ELECTRICAL CURRENT INDUCED IN AN ELECTRICAL LEAD CONDUCTOR DISPOSED WITHIN BODY TISSUE TO A PLURALITY OF ELECTRODES ELECTRICALLY COUPLED WITH THE BODY TISSUE VIA A CIRCUIT WITHIN AN END CAP ATTACHED TO THE ELECTRICAL LEAD

1502 — ROUTING THE ELECTRICAL CURRENT TO THE PLURALITY OF ELECTRODES IF THE FREQUENCY OF THE CURRENT IS WITHIN A FIRST PREDETERMINED RANGE

1504 — INHIBITING THE FLOW OF THE ELECTRICAL CURRENT TO THE PLURALITY OF ELECTRODES IF THE FREQUENCY OF THE CURRENT IS WITHIN A SECOND PREDETERMINED RANGE

FIG. 16

METHOD AND APPARATUS FOR SHUNTING INDUCED CURRENTS IN AN ELECTRICAL LEAD

FIELD OF THE INVENTION

This invention generally relates to implantable medical devices and, more specifically, to a method and apparatus for shunting electrical currents induced in an abandoned electrical lead.

DESCRIPTION OF THE RELATED ART

Since the introduction of the first implantable pacemakers in the 1960s, there have been considerable advancements in both the fields of electronics and medicine, such that there is presently a wide assortment of commercially available body-implantable electronic medical devices. The class of implantable medical devices now includes therapeutic and diagnostic devices, such as pacemakers, cardioverters, defibrillators, neural stimulators, and drug administering devices, among others. Today's state-of-the-art implantable medical devices are vastly more sophisticated and complex than their early counterparts, and are capable of performing significantly more complex tasks. The therapeutic benefits of such devices have been well proven.

Modern electrical therapeutic and diagnostic devices for the heart require a reliable electrical connection between the device and a region of the heart. Typically, an electrical contact, commonly referred to as a "lead," is used for the desired electrical connection. One type of commonly used implantable lead is a transvenous lead. Transvenous leads are generally positioned through the venous system to attach and/or electrically connect at their distal end via a tip electrode to the heart. At their proximal end, they are typically connected to the electrical therapeutic and/or diagnostic device, which may be implanted. Such leads normally take the form of a long, flexible, insulated conductor. Among the many advantages of transvenous leads is that they permit an electrical contact with the heart without physically exposing the heart itself, i.e., major thoracic surgery is not required.

The leads may have various numbers of electrodes electrically coupled to the conductors. For example, unipolar leads may have a conductor leading to and electrically coupled with an electrode at the distal tip of the lead. Bipolar leads may, for example, have one conductor leading to and electrically coupled with an electrode at the distal tip of the lead and a ring electrode disposed some distance the tip electrode. Other leads may have one or more electrode coils, for example, in addition to tip and/or ring electrodes, for delivering defibrillating shocks to a patient.

It may become desirable in certain cases to abandon a previously implanted lead in favor of a new lead. For example, the previously implanted lead may have become insufficient in its operation and, thus, a new lead is needed. Or, a new lead being different in style or type may be desirable to further the patient's care. In such situations, it is typically common practice to abandon the previously implanted lead in place, rather than explanting the lead, and to install a new, more desirable lead for use in the patient's treatment.

Generally, an abandoned lead is detached from the electrical therapeutic and/or diagnostic device and the end of the lead, previously attached to the device, is covered by a lead end cap to prevent body fluids from entering the lead body. If such body fluids are allowed to enter the lead body, an environment may be created that may foster the reproduction and spread of infectious organisms. End caps are generally made of an electrically non-conductive material (e.g., silicone rubber or the like) that serves to minimize the likelihood of low-frequency current flow through the abandoned lead. In certain situations, such low-frequency current flow may result in undesirable stimulation of the body portion to which the lead extends or cause the electrical therapeutic and/or diagnostic device to malfunction, even though the abandoned lead is no longer attached to the device.

Other advancements in medical technology have led to improved imaging technologies, for example magnetic resonance imaging (MRI). MRI generates cross-sectional images of a human body by using nuclear magnetic resonance (NMR). The MRI process begins with positioning the body to be imaged in a strong, uniform magnetic field, which polarizes the nuclear magnetic moments of protons within hydrogen molecules in the body by forcing their spins into one of two possible orientations. Then an appropriately polarized radio-frequency field, applied at resonant frequency, forces spin transitions between these orientations. The spin transitions create a signal, an NMR phenomenon, which can be detected by a receiving coil.

Further, shortwave diathermy, microwave diathermy, ultrasound diathermy, and the like have been shown to provide therapeutic benefits to patients, such as to relieve pain, stiffness, and muscle spasms; to reduce joint contractures; to reduce swelling and pain after surgery; to promote wound healing; and the like. Generally, energy (e.g., shortwave energy, microwave energy, ultrasound energy, or the like) is directed into a localized area of the patient's body.

Traditionally, however, use of these technologies have been discouraged for patients having such implanted medical devices and/or abandoned leads, as the environment produced by the MRI or diathermy apparatuses is generally considered hostile to such implantable medical devices. The energy fields, generated during the MRI or diathermy processes, may induce an electrical current in leads of implantable medical devices and/or in abandoned leads. In conventional leads, whether attached to an electrical therapeutic and/or diagnostic device or abandoned, the electrical current is typically dissipated via the lead's tip electrode into tissue adjacent the distal end of the lead. The dissipation of this electrical current may cause resistive heating in the tissue adjacent the electrode and may result in damage to the tissue in some cases.

The present invention is directed to overcoming, or at least reducing, the effects of one or more of the problems set forth above.

SUMMARY OF THE INVENTION

In one aspect of the present invention, an electrical lead end cap is provided. The electrical lead end cap includes a body defining a bore therein capable of receiving and retaining an end of an electrical lead and a connector capable of electrically coupling conductors leading to at least two electrodes.

In another aspect of the present invention, an electrical lead end cap is provided. The electrical lead end cap includes a body defining a bore therein capable of receiving and retaining an end of an electrical lead, an electrode insulatingly attached to the body, and a connector capable of electrically coupling a conductor of the electrical lead and the electrode.

In yet another aspect of the present invention, a method is provided including routing an electrical current induced in an electrical lead conductor disposed within body tissue to a plurality of electrodes, electrically coupled with the body tissue, via a circuit within an end cap attached to the electrical lead.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

As described previously, it is sometimes desirable to abandon a previously implanted lead for a pacing device, a neurostimulation device, or the like in favor of a new lead. In such situations, it is also often desirable to seal an end of the abandoned lead so that body fluids may not enter an interior portion of the lead. Further, electromagnetic fields emitted by diagnostic and/or therapeutic energy producing equipment (e.g., MRI equipment, diathermy equipment, and the like, not shown) may induce currents in the conductors within the lead, which may result in undesirable body tissue heating as they travel from lead electrodes into the body tissue.

Figure 1:
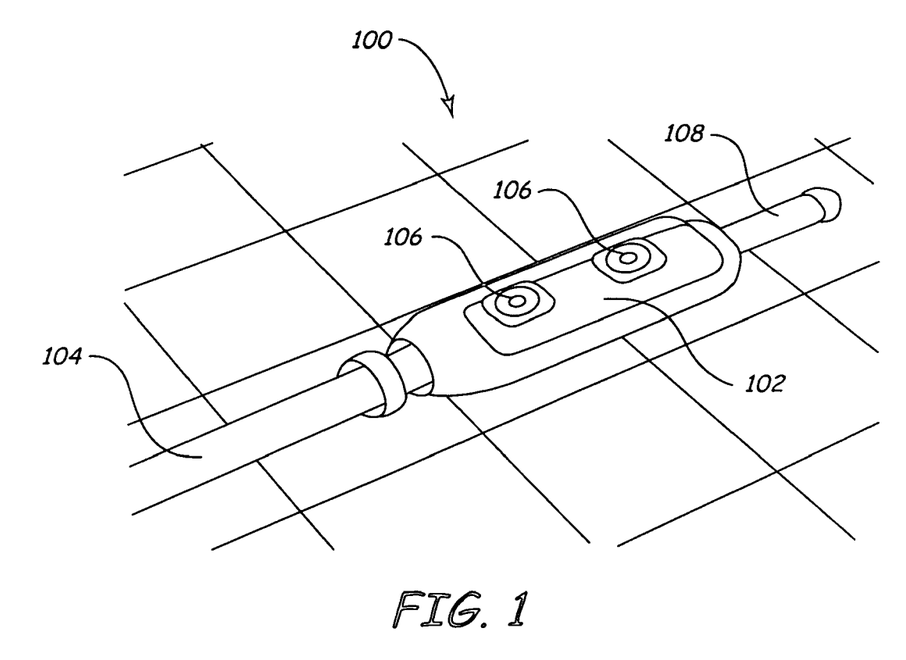
FIG. 1 is a perspective view of an end cap according to the present invention attached to an abandoned lead.
Figure 2:
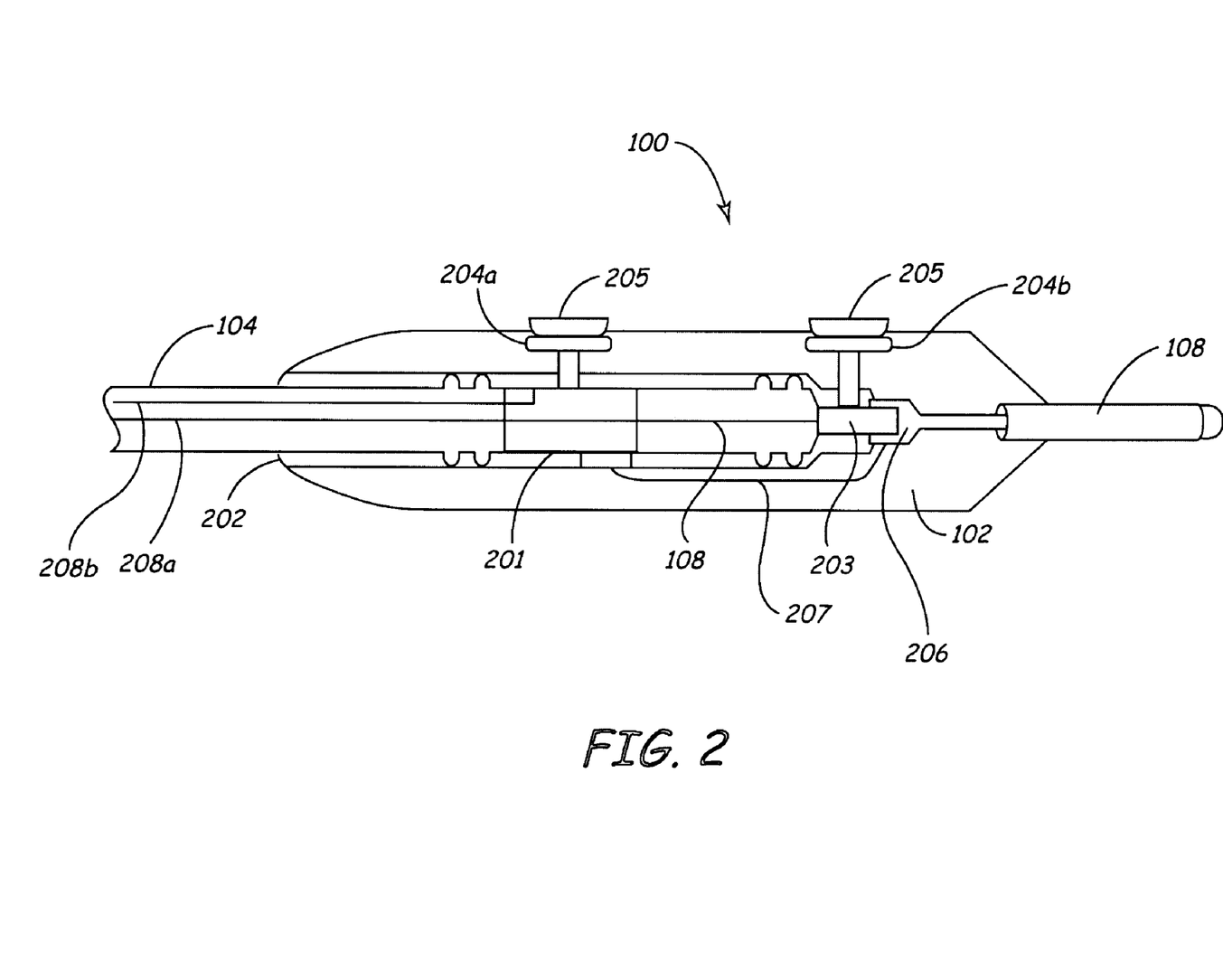
FIG. 2 is a partial cross sectional view of the end cap of FIG. 1.

An end cap 100 according to one embodiment of the present invention, as illustrated in FIGS. 1 and 2, seeks to overcome these problems. The end cap 100 includes a body 102 defining a bore 202 therein for receiving a lead 104 and sealing off access of body fluids to an interior of the lead 104. In the illustrated embodiment, the lead 104 is retained in the bore 202 by retention screws 204 disposed through openings 205 in the body 102. Plugs 206 are used to seal the openings 205 in the body 102 to prevent entry of body fluids into the end cap 100 via the openings 205. The end cap 100 further includes a connector 206 that electrically couples one or more lead conductors 208 with an electrode 108. While the connector 206 is electrically coupled with the electrode 108, the connector 206 is illustrated in FIG. 2 as being foreshortened, so that the one or more lead conductors 208 may be seen.

While FIGS. 1 and 2 illustrate an embodiment of the present invention having a cylindrical electrode, the present invention is not so limited. Rather, the end cap 100 may have an electrode of any shape and size as desired, or no electrode, as described relative to FIGS. 9–13 and discussed below.

Figure 3:
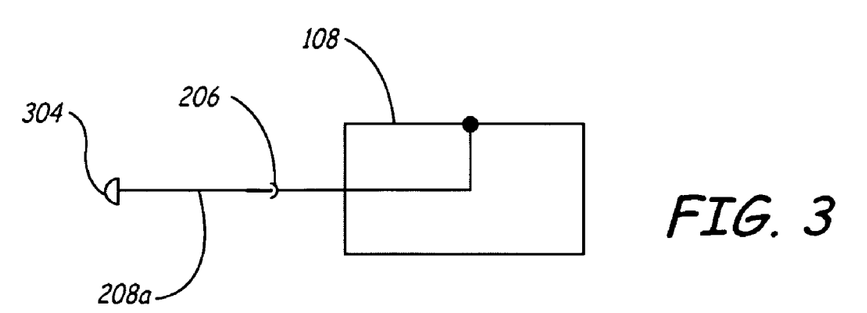
FIG. 3 is a schematic diagram of the electrode shown in FIGS. 1 and 2.

Accordingly, currents induced by the diagnostic and/or therapeutic energy producing equipment in the one or more lead conductors 208 may be conducted into surrounding body tissue via one or more lead electrodes (304) and via the electrode 108 of the end cap 100, as shown in FIG. 3. By providing additional electrode-to-tissue contact area as compared to the lead 104 omitting the end cap 100, the current is dissipated into a greater volume of tissue, thus decreasing any temperature rise adjacent to the one or more lead electrodes and the electrode 108. In leads (such as the lead 104 or the like) that have multiple lead electrodes, the lead electrodes may be electrically shorted together to achieve the desired effect.

It may be desirable, however, to prevent currents having certain frequencies (e.g., MRI frequency signals) from being conducted via the electrode 108 and flowing through the one or more lead conductors 208. For example, low-frequency currents, such as those emitted by pacing devices, neurostimulation device, or the like having frequencies generally less than about 500 hertz (Hz), may interfere with the normal function of a heart, a nerve bundle, or the like to which the abandoned lead 104 extends. Conversely, as described above, it is generally desirable for high-frequency currents, such as those induced in the one or more lead conductors 208 by electromagnetic fields emitted from diagnostic and/or therapeutic energy producing equipment, which have frequencies generally greater than about one MHz, to be routed to body tissue via the one or more lead electrodes and the electrode 108 of the end cap 100.

Figure 4:
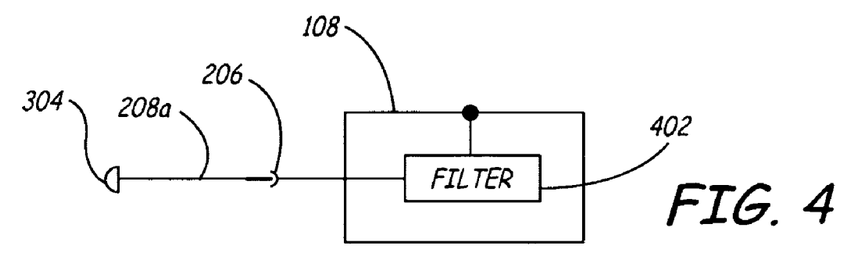
FIG. 4 is a schematic diagram of the electrode shown in FIGS. 1 and 2 having an electrical filter according to the present invention.

Thus, in the embodiment illustrated in FIG. 4, the end cap 100 further includes one or more electronic filters 402 capable of substantially blocking currents of a first frequency range from flowing through the one or more lead conductors 208 from the electrode 108 while allowing currents of a second frequency range to flow through the one or more lead conductors 208 and into body tissue via the one or more lead electrodes and the electrode 108 of the end cap 100. In one embodiment, the electronic filter 402 may block low-frequency currents from flowing through the one or more lead conductors 208 from the electrode 108 while allowing high-frequency currents to flow through the one or more lead conductors 208 and into body tissue via the one or more lead electrodes and the electrode 108 of the end cap 100.

Figure 5:
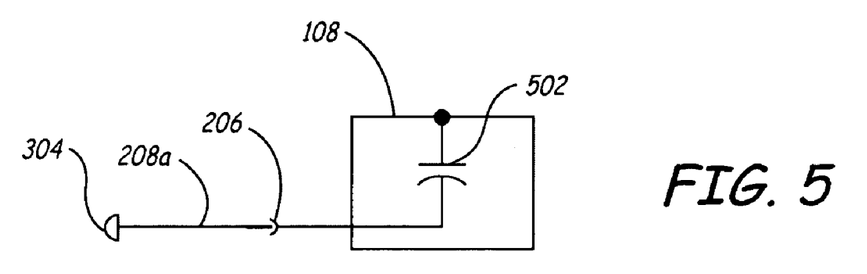
FIG. 5 is a schematic diagram of the electrode shown in FIGS. 1 and 2 having a first embodiment of the electrical filter of FIG. 3 according to the present invention.

FIG. 5 illustrates a first embodiment of the electronic filter 402 (shown in FIG. 4). The electronic filter 402 comprises a capacitor 502 connected in series with the electrode 108 and a lead electrode 304 via the lead conductor 208. Generally, the capacitor 502 has higher impedance characteristics at lower current frequencies and lower impedance at higher current frequencies. The capacitance of the capacitor 502 is selected to provide a low impedance relative to the electrode-to-tissue impedance (ranging from about 20 ohms to about 100 ohms) at frequencies characteristic of currents induced by diagnostic and/or therapeutic energy producing equipment while providing a high impedance relative to the electrode-to-tissue impedance at frequencies characteristic of currents produced by pacing devices, neurostimulation devices, and the like. In this way, lower frequency currents are substantially prevented from flowing from the electrode 108 into the lead conductor 208, while higher frequency currents, such as currents induced by diagnostic and/or therapeutic energy producing equipment, are allowed to flow from the lead conductor 208 to the electrode 108 and, to a lesser extent, to the lead electrode 304.

In one example, given a current frequency of about 64 MHz induced in a lead conductor 208 by a 1.5 tesla (T) MRI system, the capacitor 502, having a capacitance within a range of about 100 picofarads (pf) to about 1000 pf, provides an impedance within a range of about 2.5 ohms to about 25 ohms. In an operation of such a configuration coupled with a bipolar lead, the temperature rise proximate the lead electrode (not shown) may be approximately 4.9° C., while the temperature rise proximate a lead electrode of a capped lead omitting the capacitor 502 may be 16.0° C. Thus, the temperature rise proximate a lead electrode may be reduced, thereby reducing the likelihood of damage to tissue proximate the lead electrode. Further, it has been found that when the length of the lead conductor 208 is approximately equal to the wavelength of the high-frequency current, providing a low impedance termination at the electrode 108 of the end cap 100 reduces the flow of current that may be induced by antenna effects in the lead conductor 208, to the lead electrode 304 in favor of the electrode 108. In leads (such as the lead 104 or the like) that have multiple lead electrodes (such as the lead electrode 304), the lead electrodes may be electrically shorted together to achieve the desired effect.

Figure 6:
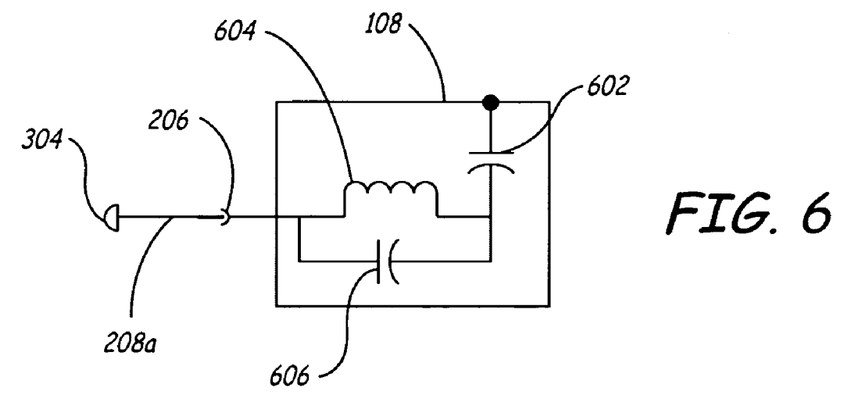
FIG. 6 is a schematic diagram of the electrode shown in FIGS. 1 and 2 having a second embodiment of the electrical filter of FIG. 3 according to the present invention.

A second embodiment of the filter 402 (shown in FIG. 4) is illustrated in FIG. 6. In this embodiment, the filter 402 includes a first capacitor 602 and an inductor 604 connected in series with the electrode 108 and the lead electrode 304 via the lead conductor 208. As described above in relation to the first embodiment of the filter 402, the first capacitor 602 generally has higher impedance characteristics at lower current frequencies and lower impedance at higher current frequencies. In this way, lower frequency currents are substantially prevented from flowing from the electrode 108 into the lead conductor 208, while higher frequency currents, such as currents induced by diagnostic and/or therapeutic energy producing equipment, are allowed to flow from the lead conductor 208 to the electrode 108 and, to a lesser extent, to the lead electrode 304.

Further, the filter 402 includes a second capacitor 606 connected in parallel with the inductor 604 to form a tuned LC network, which is used to impede currents from traveling to the lead electrode 304 due to antenna effects. In one embodiment, the capacitance of the second capacitor 606 is about 500 pf and the inductance of the inductor 604 is about 50 nanohenries (nH), thus providing high impedance to currents having frequencies of about 32 MHz and wavelengths of about 100 cm, which, in one case, is equal to about twice the length of the lead conductor 208. Accordingly, the flow of current having these properties is impeded from flowing from the lead electrode 304 into surrounding tissue. In leads (such as the lead 104 or the like) that have multiple lead electrodes (such as the lead electrode 304), the lead electrodes may be electrically shorted together to achieve the desired effect.

While one LC network (i.e., the inductor 604 and the second capacitor 606) is illustrated in FIG. 5, the present invention encompasses any configuration and/or number of LC networks. By adding more parallel LC networks in series, the frequency behavior of the filter 402 can be modified to add high impedances for other ranges of frequencies. The LC networks, as well as any other filters, may be contained within the electrode 108 or may be external to the electrode 108 and contained within the body 102 of the end cap 100.

Figure 7:
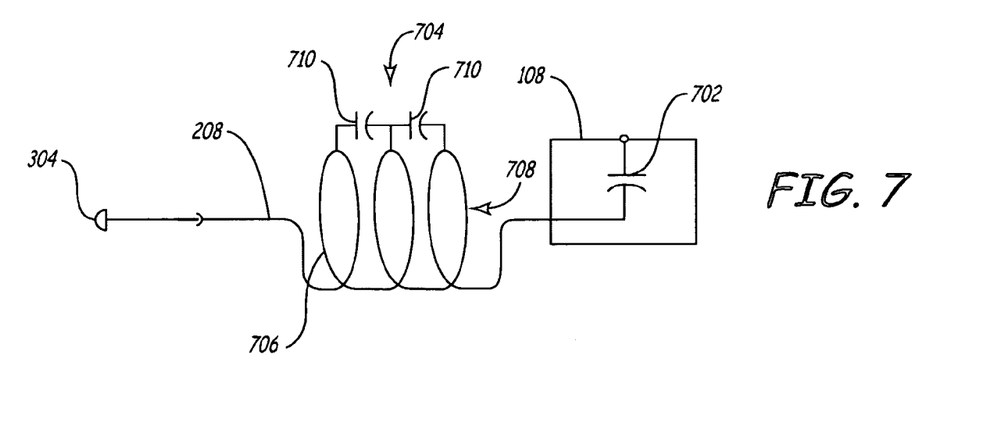
FIG. 7 is a schematic diagram of the electrode shown in FIGS. 1 and 2 having a third embodiment of the electrical filter of FIG. 3 according to the present invention.

FIG. 7 illustrates a third embodiment of the filter 402 (shown in FIG. 4). In this embodiment, the filter 402 includes a capacitor 702 and an LC network 704 connected in series between the lead electrode 304 and the electrode 108. In the illustrated embodiment, the LC network 704 is constructed using a thin wire 706 with thin insulation that, when wound into a coil 708, uses the self-capacitance (illustrated by capacitors 710) and the inductance of the coil 708 to form a resonant circuit. In one embodiment, the LC network 704 self-resonates at a frequency of about 32 MHz and the capacitor 702 provides a low impedance at a frequency of about 64 MHz. Thus, currents having frequencies of about 32 MHz (the resonant frequency of the LC network 704) are impeded from being emitted from the lead electrode 304, while currents having frequencies of about 64 MHz are allowed to flow from the electrode 108 and, to a lesser extent, from the lead electrode 304. In leads (such as the lead 104 or the like) that have multiple lead electrodes (such as the lead electrode 304), the lead electrodes may be electrically shorted together to achieve the desired effect.

While the LC network 704 illustrated in FIG. 7 includes a three-turn coil 708, the present invention encompasses a coil 708 having any number of turns and/or any other variety of inductor. By adjusting the number of turns in the coil 708, the frequency behavior of the LC network 704 can be modified to add high impedances for other ranges of frequencies. Further, multiple LC networks 704 may be used and may be contained within the electrode 108 or may be external to the electrode 108 and contained within the body 102 of the end cap 100.

Figure 8:
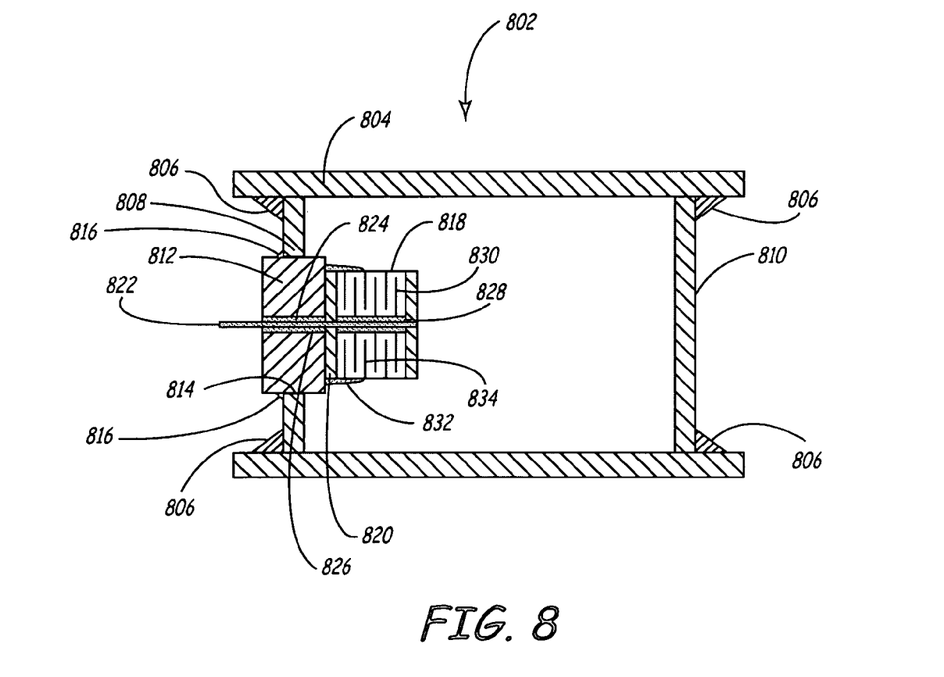
FIG. 8 is a cross-sectional view of the electrode of FIG. 4.
Figure 9:
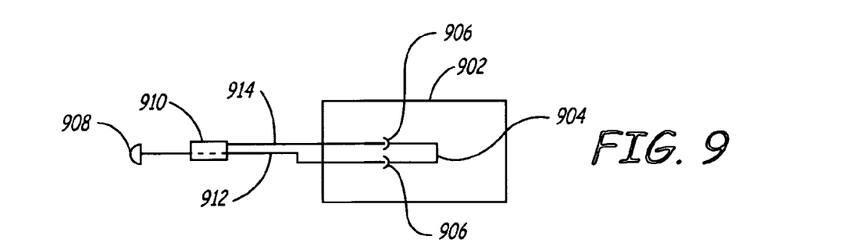
FIG. 9 is a schematic diagram of an end cap according to the present invention.

An embodiment of a construction of an electrode 802 corresponding to the electrode 108 of FIG. 5 is illustrated in FIG. 8. The electrode 802, which may, in one embodiment, be hermetically sealed, includes a tube 804 that is joined (e.g., by welds 806 or the like) to a first end portion 808 and a second end portion 810. A ferrule 812 extends through an opening 814 defined by the first end portion 808. In the illustrated embodiment, the ferrule 812 is attached to the first end portion 808 by a weld 816, sealing any space left between the ferrule 812 and the opening 814 in the first end portion 808. A capacitor 818 is spaced apart from the ferrule 812 by a dielectric spacer 820, in one embodiment, to provide electrical isolation. A pin 822 extends through the capacitor 818 and through an insulator 824 disposed in an opening 826 defined by the ferrule 812. In one embodiment, the pin 822 is adhesively attached to the capacitor 818 by an electrically conductive adhesive 828 such that a first set of plates 830 of the capacitor 818 are electrically coupled with the pin 822. The capacitor 818 is adhesively attached to the ferrule 812 by an electrically conductive adhesive 832 such that a second set of plates 834 of the capacitor 818 is electrically coupled with the ferrule 812. The electrically conductive adhesive 828 and the electrically conductive adhesive 832 may be made from the same or different adhesive materials. An end 836 of the pin 822 is connectable to the connector 206 of the end cap 100 (shown in FIG. 1).

In other embodiments corresponding to the embodiments illustrated in FIGS. 6 and 7, the electrode 108 may be constructed in a similar fashion to the electrode 802 of FIG. 8. For example, the first capacitor 602, the inductor 604, and the second capacitor 606 (shown in FIG. 6) may be disposed within the tube 804 illustrated in FIG. 8. Further, the capacitor 702, as well as the LC network 704, may be disposed within the tube 804 illustrated in FIG. 8.

While the present end cap may have an electrode (e.g., the electrode 108 of FIGS. 1–7, the electrode 802 of FIG. 8, or the like), it may rather electrically couple two or more electrodes of a lead. According to one embodiment, illustrated in FIG. 9, an end cap 902 includes a circuit 904 electrically coupling two or more contacts 906. When a lead is inserted into the end cap 902, as described in relation to FIGS. 1 and 2, a first lead electrode 908 is electrically coupled with a second lead electrode 910 via lead conductors 912, 914, respectively.

As described previously, it may be desirable in certain situations to prevent currents having certain frequencies (e.g., MRI frequency signals) from being conducted via the electrodes 908, 910 and flowing through the one or more lead conductors 912, 914. In the embodiment illustrated in FIG. 10, the circuit 904 further includes one or more electronic filters 1002 capable of substantially blocking currents of a first frequency range from flowing through the lead conductors 912, 914 from the lead electrodes 908, 910 while allowing currents of a second frequency range to flow through the lead conductors 912, 914 and into body tissue via the lead electrodes 908, 910.

Figure 10:
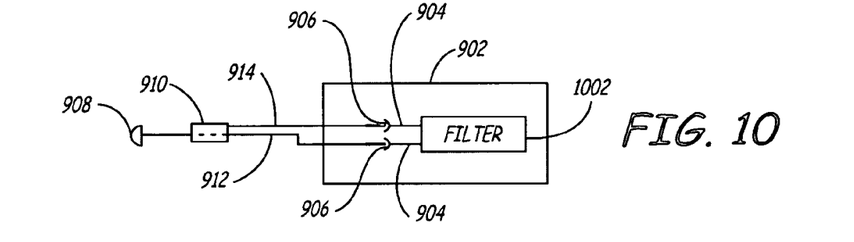
FIG. 10 is a schematic diagram of an end cap according to the present invention having an electrical filter.
Figure 11:
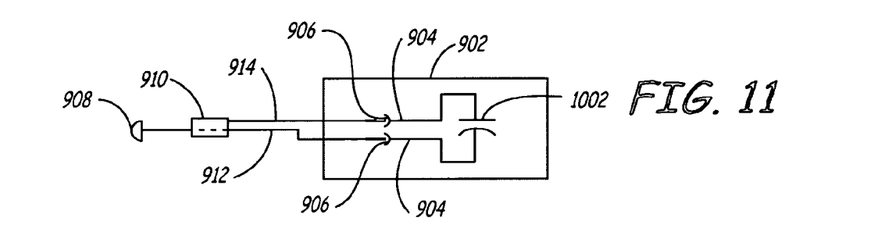
FIG. 11 is a schematic diagram of an end cap according to the present invention having a first embodiment of the electrical filter of FIG. 10.

FIG. 11 illustrates a first embodiment of the electronic filter 1002 (shown in FIG. 10). The electronic filter 1002 comprises a capacitor 1102 connected in series with the first lead electrode 908 and the second lead electrode 910 via the lead conductors 912, 914. Generally, as in the embodiment of FIG. 5, the capacitor 1102 has higher impedance characteristics at lower current frequencies and lower impedance at higher current frequencies. The capacitance of the capacitor 1102 is selected to provide a low impedance relative to the electrode-to-tissue impedance (ranging from about 20 ohms to about 100 ohms) at frequencies characteristic of currents induced by diagnostic and/or therapeutic energy producing equipment while providing a high impedance relative to the electrode-to-tissue impedance at frequencies characteristic of currents produced by pacing devices, neurostimulation devices, and the like. In this way, lower frequency currents are substantially prevented from flowing from either of the lead electrodes 908, 910 into the lead conductors 912, 914, while higher frequency currents, such as currents induced by diagnostic and/or therapeutic energy producing equipment, are allowed to flow from the lead conductors 912, 914 to the lead electrodes 901, 910.

Figure 12:
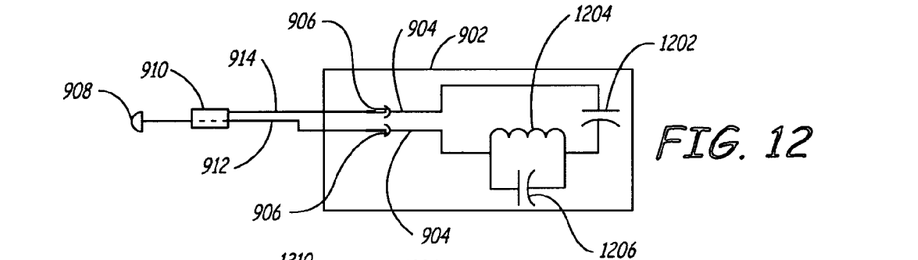
FIG. 12 is a schematic diagram of an end cap according to the present invention having a second embodiment of the electrical filter of FIG. 10.

A second embodiment of the filter 1002 (shown in FIG. 10) is illustrated in FIG. 12. In this embodiment, the filter 1002 includes a first capacitor 1202 and an inductor 1204 connected in series with the lead electrode 908, 910 via the lead conductors 912, 914. As described above in relation to the first embodiment of the filter 1002, the first capacitor 1202 generally has higher impedance characteristics at lower current frequencies and lower impedance at higher current frequencies. In this way, lower frequency currents are substantially prevented from flowing from either of the lead electrodes 908, 910 into the lead conductors 912, 914, while higher frequency currents, such as currents induced by diagnostic and/or therapeutic energy producing equipment, are allowed to flow from the lead conductors 912, 914 to the lead electrode 908, 910.

Further, the filter 1002 includes a second capacitor 1206 connected in parallel with the inductor 1204 to form a tuned LC network, which is used to impede currents from traveling to the lead electrodes 908, 910 due to antenna effects. In leads (such as the lead 104 or the like) that have more than two lead electrodes (such as the lead electrodes 912, 914), more than two lead electrodes may be electrically shorted together to achieve the desired effect.

While one LC network (i.e., the inductor 1204 and the second capacitor 1206) is illustrated in FIG. 12, the present invention encompasses any configuration and/or number of LC networks. By adding more parallel LC networks in series, the frequency behavior of the filter 1002 can be modified to add high impedances for other ranges of frequencies.

Figure 13:
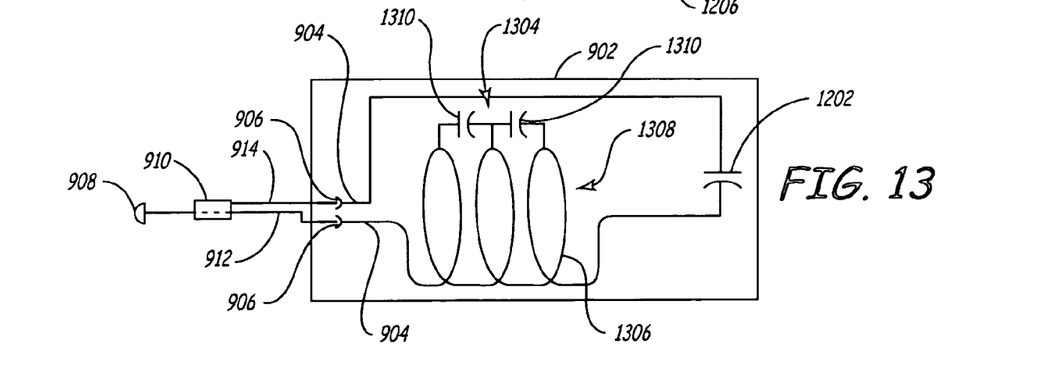
FIG. 13 is a schematic diagram of an end cap according to the present invention having a third embodiment of the electrical filter of FIG. 10.

FIG. 13 illustrates a third embodiment of the filter 1002 (shown in FIG. 10). In this embodiment, the filter 1002 includes a capacitor 1302 and an LC network 1304 connected in series between the lead electrodes 908, 910. In the illustrated embodiment, the LC network 1304 is constructed using a thin wire 1306 with thin insulation that, when wound into a coil 1308, uses the self-capacitance (illustrated by capacitors 1310) and the inductance of the coil 1308 to form a resonant circuit. In leads (such as the lead 104 or the like) that have more than two lead electrodes (such as the lead electrodes 912, 914), more than two lead electrodes may be electrically shorted together to achieve the desired effect.

While the LC network 1304 illustrated in FIG. 13 includes a three-turn coil 1308, the present invention encompasses a coil 1308 having any number of turns and/or any other variety of inductor. By adjusting the number of turns in the coil 1308, the frequency behavior of the LC network 1304 can be modified to add high impedances for other ranges of frequencies. Further, multiple LC networks 1304 may be used.

It should also be noted that, while certain types, sizes, and shapes of electrodes are illustrated herein, the present invention is not limited to the depicted types, shapes, and sizes of electrodes. Rather, any type, shape, and size electrode desired, whether an end cap electrode or a lead electrode, is within the scope of the present invention.

Figure 14:
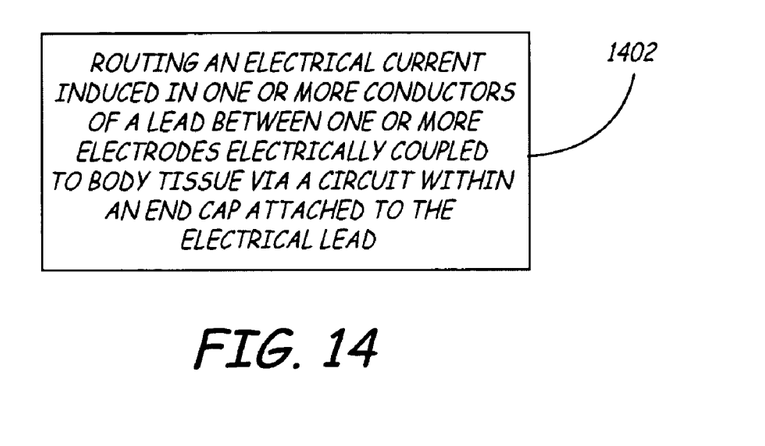
FIG. 14 is a flow chart of a first embodiment of a method according to the present invention.
Figure 15:
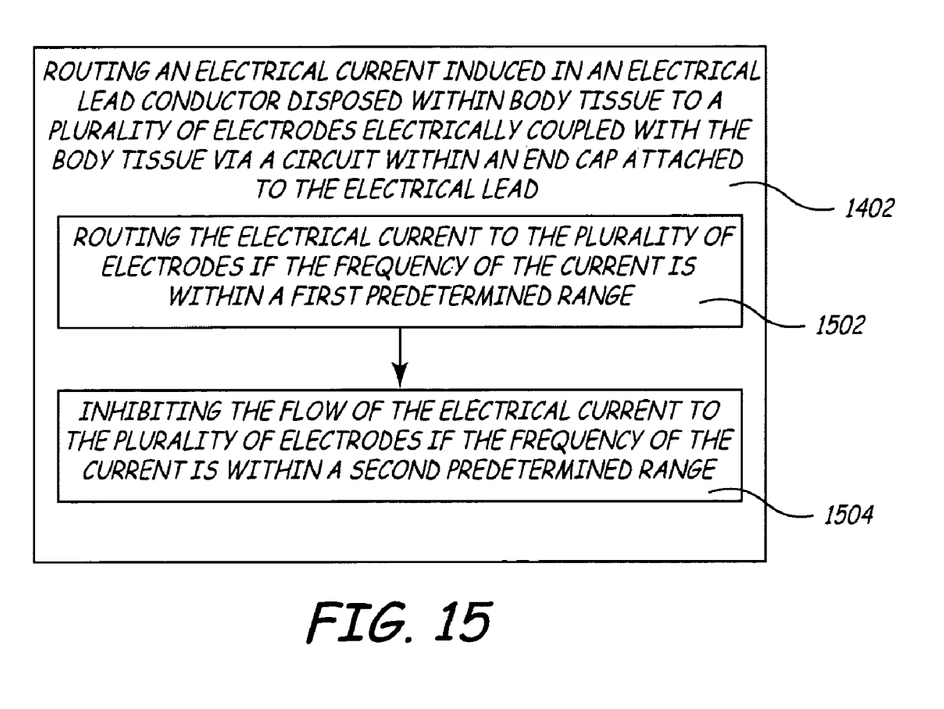
FIG. 15 is a flow chart of a second embodiment of a method according to the present invention.

FIG. 14 illustrates a first embodiment of a method according to the present invention. In the illustrated embodiment, the method includes routing an electrical current induced in a conductor disposed within body tissue to a plurality of electrodes electrically coupled with the body tissue via a circuit within an end cap attached to a lead enclosing the conductor (block 1402). The electrodes may be lead electrodes or may be one or more lead electrodes and an electrode of the end cap. In a second embodiment, illustrated in FIG. 15, routing an electrical current (block 1402) further comprises routing the electrical current to the plurality of electrodes if the frequency of the current is within a first predetermined range (block 1502) and inhibiting the flow of the electrical current to the plurality of electrodes if the frequency of the current is within a second predetermined range (block 1504).

Figure 16:
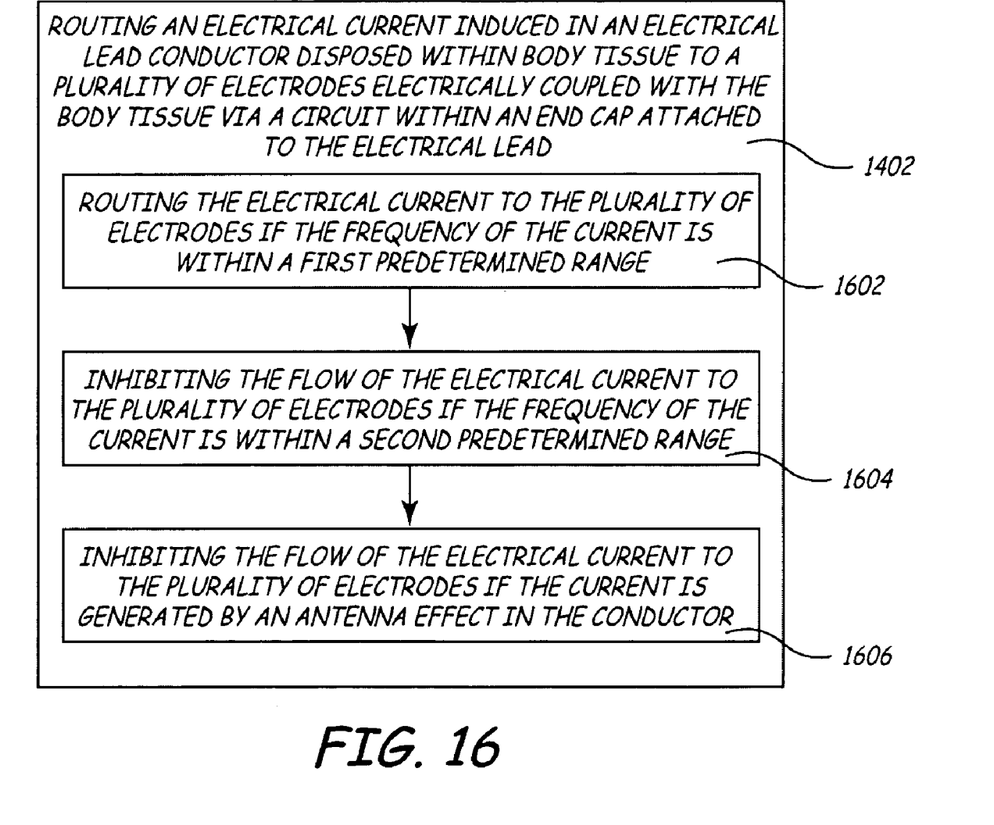
FIG. 16 is a flow chart of a third embodiment of a method according to the present invention.

In a third embodiment of the present invention, illustrated in FIG. 16, routing an electrical current (block 1402) further comprises routing the electrical current to the plurality of electrodes if the frequency of the current is within a first predetermined range (block 1602), inhibiting the flow of the electrical current to the plurality of electrodes if the frequency of the current is within a second predetermined range (block 1604), and inhibiting the flow of the electrical current to the plurality of electrodes if the current is generated by an antenna effect in the conductor (block 1606).

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. In particular, every range of values (of the form, "from about a to about b," or, equivalently, "from approximately a to b," or, equivalently, "from approximately a–b") disclosed herein is to be understood as referring to the power set (the set of all subsets) of the respective range of values, in the sense of George Cantor. Accordingly, the protection sought herein is as set forth in the claims below.

What is claimed is:

1. An electrical lead end cap, comprising:
   a body defining a bore therein capable of receiving and retaining an end of an electrical lead; and
   a connector capable of electrically coupling conductors leading to at least two electrodes;
   wherein a first electrode of the at least two electrodes is a lead electrode and a second electrode of the at least two electrodes is an electrode of the electrical lead end cap.

2. An electrical lead end cap, according to claim 1, further comprising a capacitor coupled to the connector and being capable of impeding a current having a first frequency from flowing through the conductors when the conductors are coupled and capable of allowing a current having a second frequency to flow through the filter when the conductors are coupled.

3. An electrical lead end cap, according to claim 2, wherein:
   a first electrode of the at least two electrodes is a lead electrode and a second electrode of the at least two electrodes is an electrode of the lead end cap;
   the second electrode further comprises a hermetically sealed enclosure; and
   the capacitor is disposed within the hermetically sealed enclosure.

4. An electrical lead end cap, according to claim 1, further comprising a first capacitor and an LC network electrically coupled to the connector, wherein:
   the first capacitor is capable of impeding a current having a first frequency from flowing through the conductors when the conductors are coupled and is capable of allowing a current having a second frequency to flow through the conductors when the conductors are coupled; and
   the LC network is capable of impeding a current having a third frequency from flowing through the conductors when the conductors are coupled.

5. An electrical lead end cap, according to claim 4, wherein:
   a first electrode of the at least two electrodes is a lead electrode and a second electrode of the at least two electrodes is an electrode of the lead end cap;
   the second electrode further comprises a hermetically sealed enclosure; and
   the capacitor and the LC network are disposed within the hermetically sealed enclosure.

6. An electrical lead end cap, according to claim 1, further comprising:
   a first capacitor electrically coupled to the connector;
   an inductor electrically coupled to the connector; and
   a second capacitor electrically coupled in parallel with the inductor,
   wherein:
   the first capacitor is capable of impeding a current having a first frequency from flowing through the conductors when the conductors are coupled and is capable of allowing a current having a second frequency to flow through the conductors when the conductors are coupled; and
   the inductor in combination with the second capacitor are capable of impeding a current having a third frequency from flowing through the conductors when the conductors are coupled.

7. An electrical lead end cap, according to claim 6, wherein:
   a first electrode of the at least two electrodes is a lead electrode and a second electrode of the at least two electrodes is an electrode of the lead end cap;
   the second electrode further comprises a hermetically sealed enclosure; and
   the first capacitor, the inductor, and the second capacitor are disposed within the hermetically sealed enclosure.

8. An electrical lead end cap, according to claim 1, further comprising:
   a capacitor electrically coupled to the connector; and
   an inductor having self capacitance electrically coupled to the connector,
   wherein:
   the capacitor is capable of impeding a current having a first frequency from flowing through the conductors when the conductors are coupled and is capable of allowing a current having a second frequency to flow through the conductors when the conductors are coupled; and the inductor is capable of impeding a current having a third frequency from flowing through the conductors when the conductors are coupled.

9. An electrical lead end cap, according to claim 8, wherein:
a first electrode of the at least two electrodes is a lead electrode and a second electrode of the at least two electrodes is an electrode of the lead end cap;
the second electrode further comprises a hermetically sealed enclosure; and
the capacitor and the inductor are disposed within the hermetically sealed enclosure.

10. An electrical lead end cap, according to claim 1, wherein the electrical lead further comprises:
an elongate body having a proximal end portion and a distal end portion; and
a lead electrode disposed adjacent and joined to the distal end portion of the elongate body, wherein:
the conductor of the electrical lead extends between the proximal end portion and the distal end portion of the elongate body and is electrically coupled to the lead electrode; and
the proximal end portion is capable of being received and retained in the bore defined by the body of the electrical lead end cap.

11. An electrical lead end cap, comprising:
a body defining a bore therein capable of receiving and retaining an end of an electrical lead;
a connector capable of electrically coupling conductors leading to at least two electrodes; and
an electrical filter coupled to the connector and being capable of impeding a current having a first frequency from flowing through the conductors when the conductors are coupled and capable of allowing a current having a second frequency to flow through conductors when the conductors are coupled.

12. An electrical lead end cap, according to claim 11, wherein:
a first electrode of the at least two electrodes is a lead electrode and a second electrode of the at least two electrodes is an electrode of the lead end cap; and
the second electrode further comprises a hermetically sealed enclosure and the electrical filter is disposed within the hermetically sealed enclosure.

13. An end cap for a proximal end of an abandoned implanted electrical lead having a distal end electrode attached to a tissue location, comprising:
a body having a bore therein to receive a proximal end of an implanted electrical lead and seal access of body fluids to its interior;
a connector disposed within the body and coupled to an electrical conductor within the proximal end of the abandoned implanted electrical lead; and
an electrode coupled to the connector and having a tissue surface contact area greater than a tissue surface contact area of the electrical conductor within the proximal end of the electrical lead.

14. An electrical lead end cap, according to claim 13, wherein the electrode further comprises a hermetically sealed enclosure, wherein the electrical lead end cap further comprises:
a pin electrically coupled with the connector and extending into the hermetically sealed enclosure such that the pin is electrically insulated from the hermetically sealed enclosure; and
an electrical filter having a first connection electrically coupled with the pin and a second connection electrically coupled with the hermetically sealed enclosure, wherein the electrical filter is disposed within the hermetically sealed enclosure.

15. An electrical lead end cap, according to claim 13, wherein the electrode further comprises a hermetically sealed enclosure, wherein the electrical lead end cap further comprises:
a pin electrically coupled with the connector and extending into the hermetically sealed enclosure such that the pin is electrically insulated from the hermetically sealed enclosure; and
a capacitor having a first connection electrically coupled with the pin and a second connection electrically coupled with the hermetically sealed enclosure, wherein the capacitor is disposed within the hermetically sealed enclosure.

16. An electrical lead end cap, according to claim 13, wherein the electrode further comprises a hermetically sealed enclosure, wherein the electrical lead end cap further comprises:
a pin electrically coupled with the connector and extending into the hermetically sealed enclosure such that the pin is electrically insulated from the hermetically sealed enclosure;
an LC network disposed within the hermetically sealed enclosure and having a first connection electrically coupled with the pin and a second connection; and
a capacitor disposed within the hermetically sealed enclosure and having a first connection electrically coupled with the LC network and a second connection electrically coupled with the hermetically sealed enclosure.

17. An electrical lead end cap, according to claim 13, wherein the electrode further comprises a hermetically sealed enclosure, wherein the electrical lead end cap further comprises:
a pin electrically coupled with the connector and extending into the hermetically sealed enclosure such that the pin is electrically insulated from the hermetically sealed enclosure;
an inductor disposed within the hermetically sealed enclosure and having a first connection electrically coupled with the pin and a second connection; and
a capacitor disposed within the hermetically sealed enclosure and having a first connection electrically coupled with the second connection of the inductor and a second connection electrically coupled with the hermetically sealed enclosure.

18. An electrical lead end cap, according to claim 13, wherein the electrode further comprises a hermetically sealed enclosure, wherein the electrical lead end cap further comprises:
a pin electrically coupled with the connector and extending into the hermetically sealed enclosure such that the pin is electrically insulated from the hermetically sealed enclosure;
an inductor disposed within the hermetically sealed enclosure and having a first connection electrically coupled with the pin and a second connection;
a first capacitor disposed within the hermetically sealed enclosure and having a first connection electrically coupled with the second connection of the inductor and a second connection electrically coupled with the hermetically sealed enclosure; and
a second capacitor disposed within the hermetically sealed enclosure and being electrically coupled in parallel with the inductor.

19. An electrical lead end cap, according to claim 13, wherein the electrode further comprises a hermetically sealed enclosure, wherein the electrical lead end cap further comprises:

a pin electrically extending into the hermetically sealed enclosure such that the pin is electrically insulated from the hermetically sealed enclosure;

a capacitor having a first connection electrically coupled with the pin and a second connection electrically coupled with the hermetically sealed enclosure, wherein the capacitor is disposed within the hermetically sealed enclosure; and an inductor having self-capacitance and being disposed within the body and external to the hermetically sealed enclosure, wherein the inductor is electrically coupled with the pin and the connector.

20. A method comprising routing an electrical current induced in an electrical lead conductor disposed within body tissue to a plurality of electrodes, electrically coupled with the body tissue, via a circuit within an end cap attached to a proximal end of an abandoned implanted electrical lead having a distal end electrode attached to a tissue location.

21. A method, according to claim 20, wherein routing the electrical current further comprises routing the electrical current to a lead electrode and to an end cap electrode.

22. A method, according to claim 20, wherein routing the electrical current further comprises routing the electrical current to a plurality of lead electrodes.

23. A method, according to claim 20, wherein routing the electrical current further comprises:

routing the electrical current to the plurality of electrodes if the frequency of the current is within a first predetermined range; and inhibiting the flow of the electrical current to the plurality of electrodes if the frequency of the current is within a second predetermined range.

24. A method, according to claim 20, wherein selectively routing the electrical current further comprises:

routing the electrical current to the plurality of electrodes if the frequency of the current is within a first predetermined range;

inhibiting the flow of the electrical current to the plurality of electrodes if the frequency of the current is within a second predetermined range; and inhibiting the flow of the electrical current to the plurality of electrodes if the current is generated by an antenna effect in the conductor.

25. An apparatus comprising means for routing an electrical current induced in an electrical lead conductor disposed within body tissue to a plurality of electrodes, electrically coupled with the body tissue, via a circuit within an end cap attached to the electrical lead.

26. An apparatus, according to claim 25, wherein the means for routing the electrical current further comprises means for routing the electrical current to a lead electrode and to an end cap electrode.

27. An apparatus, according to claim 25, wherein the means for routing the electrical current further comprises means for routing the electrical current to a plurality of lead electrodes.

28. An apparatus, according to claim 25, wherein the means for routing the electrical current further comprises:

means for routing the electrical current to the plurality of electrodes if the frequency of the current is within a first predetermined range; and means for inhibiting the flow of the electrical current to the plurality of electrodes if the frequency of the current is within a second predetermined range.

29. An apparatus, according to claim 25, wherein the means for routing the electrical current further comprises:

means for routing the electrical current to the plurality of electrodes if the frequency of the current is within a first predetermined range;

means for inhibiting the flow of the electrical current to the plurality of electrodes if the frequency of the current is within a second predetermined range; and means for inhibiting the flow of the electrical current to the plurality of electrodes if the current is generated by an antenna effect in the conductor.

\* \* \* \* \*